United States Patent [19]

Carmody

[11] Patent Number: 5,225,187
[45] Date of Patent: Jul. 6, 1993

[54] PROCESS FOR PREPARING CONCENTRATED ALUMINUM-ZIRCONIUM SOLUTIONS

[75] Inventor: Walter J. Carmody, Port Jervis, N.Y.

[73] Assignee: Somerville Technology Group, Inc., Somerset, N.J.

[21] Appl. No.: 655,602

[22] Filed: Feb. 15, 1991

[51] Int. Cl.$^5$ .......................... A61K 7/34; A61K 7/38
[52] U.S. Cl. ........................ 424/66; 424/57; 424/65; 424/68; 424/617; 514/492; 556/27
[58] Field of Search ............... 424/617, 66, 47, 65, 424/68; 514/492; 556/27

[56] References Cited

U.S. PATENT DOCUMENTS

| | | | |
|---|---|---|---|
| 2,814,584 | 12/1957 | Daley | 424/66 |
| 2,854,382 | 9/1958 | Grad | 424/66 |
| 2,906,668 | 9/1959 | Beckman | 424/66 |
| 3,792,068 | 2/1974 | Luedders et al. | 424/47 |
| 4,028,390 | 6/1977 | Rubino | 556/27 |
| 4,148,812 | 4/1979 | Rubino | 556/55 |
| 4,331,609 | 5/1982 | Orr | 556/27 |
| 4,985,238 | 1/1991 | Tanner et al. | 424/66 |

FOREIGN PATENT DOCUMENTS 0256831  8/1987  European Pat. Off. ............ 25/4

OTHER PUBLICATIONS

Chemical Abstracts 99:40611a (1983).

Primary Examiner—Allen J. Robinson
Assistant Examiner—John D. Pak
Attorney, Agent, or Firm—Kenneth P. Glynn

[57] ABSTRACT

This invention pertains to a process for preparing concentrated aluminum-zirconium-glycine solutions by forming a zirconium chloride complex, adding glycine to the complex and forming coordinate bonds between the zirconium chloride complex and the glycine and blending the resulting mixture with an aqueous aluminum chlorohydrate solution. Solutions which contain 45–50% solids can be produced. The solutions have shown to be stable at room temperature for greater than 3 months.

5 Claims, No Drawings

PROCESS FOR PREPARING CONCENTRATED ALUMINUM-ZIRCONIUM SOLUTIONS

BACKGROUND OF THE INVENTION

It is well known in the art to produce aluminum-zirconium glycine solutions. However, these solutions are typically limited to concentrations of 40% solids or less. Solutions which contain more than 40% solids produced by method known in the art typically gel or become extremely viscous within a short period of time after their formation. Because of this commercially available solutions are typically limited to 35 weight percent solids or less.

Methods which are known in the art for producing aluminum-zirconium glycine solutions include, U.S. Pat. No. 2,814,584 to Daley which teaches Buffered Antiperspirant Compositions containing 5 to 50 weight percent of the antiperspirant constituents. However, the preferred range is 10 to 30 weight percent. The solutions are formed by blending a hafnium or zirconium salt, a basic aluminum salt, water and urea.

U.S. Pat. No. 2,854,382 to Grad teaches Zirconyl Hydroxy Chloride Antiperspirant Compositions containing 5 to 30% (total) of zirconyl hydroxy chloride and aluminum chlorhydroxide. However, even at 30% solids, gelling is a problem and high amounts of glycine must be added to prevent the gelling. To prevent gelling of a 30% solids solution, approximately 17.5% by weight of glycine is required. The compositions are formed by blending the desired amounts of zirconyl hydroxy chloride, aluminum chlorhydroxide, glycine and water.

U.S. Pat. No. 2,906,688 to Beekman teaches solutions of zirconyl and aluminum halohydroxy complexes. These solutions can contain up to 40% of the complex as shown in their Example I. The complexes are formed by mixing a zirconium oxyhalide and aluminum hydroxy halide and heating the mixture with agitation until a liquid results. This patent does not teach the use of glycine to buffer or add stability to the solutions.

U.S. Pat. No. 4,148,812 to Rubino et al. teaches a method for making basic zirconium-amino acid gels by reacting a water soluble salt of an amino acid and water soluble zirconium salt to form a precipitate and recovering the precipitate which is a gel. The basic zirconium-amino acid gels are then used to form complexes with conventional aluminum and/or zirconium antiperspirant systems. Rubino does not teach that the complexes are stable at higher solids concentrations in the final complex.

U.S. Pat. No. 4,028,390 to Rubino teaches astringent complexes produced from an aluminum compound and a basic zirconium carbonate gel. These complexes can also contain glycine. The method taught in U.S. Pat. No. 4,028,390 for forming the astringent complexes is to add the glycine to the aluminum compound and then add the zirconium carbonate and heat to form the complex. This patent does not teach a method for combining zirconium carbonate and glycine and heating them to directly form coordinate bonds between the zirconium and glycine prior to complexing with the aluminum compound. Further this patent only teaches solution which contain 5 to 20 weight percent (solids basis) of the complex.

U.S. Pat. No. 4,331,609 to Orr teaches aqueous solution-stable antiperspirant complexes comprising an aluminum compound, a zirconium compound, a water soluble neutral amino acid and an inorganic acidic compound. The solutions comprise 32 to 38% by weight of solids, exclusive of the neutral amino acid present. The solutions are formed by mixing the components together.

It is an object of this invention to show a method for producing stable, concentrated aluminum-zirconium glycine solutions.

It is further an object of this invention to show stable, aqueous aluminum-zirconium glycine solutions with contain 45 to 50 weight percent solids.

SUMMARY OF THE INVENTION

This invention pertains to a process for preparing concentrated aluminum-zirconium-glycine solutions by forming a zirconium chloride complex, adding glycine to the complex and forming coordinate bonds between the zirconium chloride complex and the glycine and blending the resulting mixture with an aqueous aluminum chlorohydrate solution. Solutions which contain 45-50% solids can be produced. The solutions have shown to be stable at room temperature for greater than 3 months.

THE INVENTION

The instant invention pertains to a method for making concentrated aqueous solutions of aluminum-zirconium-glycine, sometimes known in the art as aluminum-zirconium tetrachlorhydrex-gly or aluminum-zirconium trichlorhydrex-gly. The solutions of the instant invention contain 45 to 50 weight percent of solids. The process for forming the concentrated aluminum-zirconium solutions comprises (1) forming a zirconium chloride complex; (2) adding glycine to the complex and forming coordinate bonds between the zirconium and glycine; and (3) blending the resulting zirconium-glycine solution with an aqueous aluminum chlorohydrate solution. The aluminum-zirconium glycine solutions are stable at room temperature for greater than 3 months.

Stability of the solution can be defined by the viscosity of the aluminum-zirconium glycine solution. The aluminum-zirconium glycine solutions are considered stable when the viscosity has a value of less than 150 centipoise. The solutions are typically stable for at least 3 months when stored at room temperature.

The zirconium chloride complex is produced by heating an aqueous zirconium chloride solution until the complex is formed. The zirconium chloride complex can be formed by one of several methods. The first method comprises producing a zirconium chloride solution by reacting zirconium carbonate with aqueous hydrochloric acid. The zirconium chloride solution is then heated to form the complex. Another method for preparing the zirconium chloride complex is to take a commercially available zirconium hydroxychloride solution and heat that until the complex is formed. Another method for producing the zirconium chloride complex is to react a mixture of zirconium carbonate and zirconium oxychloride with an aqueous hydrochloric acid solution to produce a zirconium chloride solution. The resulting zirconium chloride solution is then heated to form the complex. Another method comprises reacting zirconium oxychloride with aqueous hydrochloric acid and heating the resulting zirconium chloride solution until the complex is formed.

The overall method for producing the zirconium chloride complex comprises taking a zirconium chloride solution and heating that to form the complex. The zirconium chloride solution is heated to a temperature of greater than 50° C. but less than 100° C. at atmospheric pressure. The preferred temperature at which to heat the solution is 90° to 95° C. at atmospheric pressure. At pressures above or below atmospheric the temperature conditions may be different but readily determinable by one skilled in the art.

The time the zirconium chloride solution is heated to form the complex will depend on the temperature used in the process. Typically ½ hour is sufficient at 90° to 95° C. to form the complex. Lower temperatures will typically take a longer time. It is preferred to maintain agitation during the heating period.

The zirconium chloride complex is produced as an aqueous solution. The zirconium chloride complex solutions useful in the instant invention are typically comprised of 17 to 20 weight percent zirconium (elemental basis) and 7 to 10 weight percent chlorine.

Zirconium carbonate, which may used in the formation of the zirconium chloride complex, may be further exemplified by compounds having the formula $$Zr(OH)_{4-2x}(CO_3)_x$$

wherein x is greater than 0 but less than 2 and need not be an integer. The formula is greatly simplified and various polymeric and water containing forms are more probable. The zirconium carbonates are typically represented by the formulas $Zr(O)CO_3$ or $Zr(OH)_2CO_3$. It should also be understood that the zirconium carbonates may also include bicarbonate groups ($HCO_3$) in addition to or in place of the carbonate groups. Zirconium carbonate is well known and commercially available.

Zirconium oxychloride, another possible compound used in the formation of the zirconium chloride complex, may be represented by $ZrOCl_2$ or $Zr(OH)_2Cl_2$. These formulas are greatly simplified and are intended to represent and include compounds having coordinated and/or bound water in various quantities, as well as polymers, mixtures, and complexes of the above. Zirconium oxychloride is well known and commercially available.

Zirconium hydroxychloride, another compound that may be used in the formation of the zirconium chloride complex, may be represented by $Zr(OH)_3Cl$ or $ZrO(OH)Cl$. As previously stated, these formulas are greatly simplified and are intended to represent and include compounds having coordinated and/or bound water in various quantities, as well as polymers, mixtures, and complexes of the above. Zirconium hydroxychloride is well known and commercially available.

After the formation of the zirconium chloride complex, glycine is added. The zirconium chloride complex solution should be at a temperature of 40° C. to 75° C. during the addition of the glycine. It is preferred that the solution be at a temperature of 50° to 70° C. during the addition of the glycine. The zirconium chloride complex and the glycine are mixed for a period of time such that the glycine is evenly dispersed in the solution. The amount of glycine added is dependent on the amount of zirconium present. The final solution should contain a Zirconium:Glycine atomic ratio of 0.8:1 to 1.2:1, preferably appriximately 1:1. The amount of glycine added is typically 13 to 15 weight percent of the total solution.

It is theorized that when the glycine is added to the zirconium chloride complex at a temperature greater than 50° C. that coordinate bonds form between the zirconium and glycine. It is further theorized that the presence of these coordinate bonds allows the formation of stable, concentrated solutions.

After the addition of the glycine the zirconium-glycine solution can be analyzed by size exclusion chromatography to ensure that there has been sufficient complexing/coordination to be useful in the formation of a stable, concentrated aluminum-zirconium solution. To be useful in the formation of a stable, concentrated aluminum-zirconium solution, the zirconium-glycine solution have at least 32 to 100 area percent of Peaks 1&2, preferably 38 to 100 area percent of Peaks 1&2.

After the addition of the glycine, the resulting zirconium-glycine solution can be mixed with an aqueous aluminum chlorohydrate solution. Any aqueous aluminum chlorohydrate solution can be used however, to achieve the object of this invention the aluminum chloride solution should contain 50% by weight of the aluminum chlorohydrate (solids). The aqueous aluminum chlorohydrate which contains 50 weight percent solids and the zirconium-glycine solution can be blended at 1 part of aluminum chlorohydrate solution for every part of zirconium-glycine solution or 3 parts of aluminum chlorohydrate solution for every 2 parts of zirconium-glycine solution to produce a final solution containing 45 to 50% solids.

The aluminum chlorohydrate contained in the aqueous solution, blended with the zirconium-glycine solution is typically represented by the formula $$Al_x(OH)_yCl_z$$

wherein $\frac{1}{3} \leq x/z \leq 2.2/1$; and y has the value of 0 to 5.6. The solutions can contain up to 55 weight percent of the aluminum chlorohydrate. However, those containing 50 weight percent are the most useful to form the concentrated aluminum-zirconium glycine solutions of this invention.

The final aluminum-zirconium glycine composition maybe represented by the formula $$Al_aZr_b(OH)_cCl_d$$

wherein a:b is 3.4:1 to 3.8:1 and $3a+4b=c+d$. The final aluminum-zirconium glycine composition typically has a metals content of 14 to 16.6 weight percent and a solution concentration of 45 to 50 percent by weight solids. The chloride ranges from 7.5 to 10 percent and the glycine from 5.5 to 7.1 percent. The concentrated aluminum-zirconium glycine solutions have a stable viscosity of less than 150 centipoise over a period of at least 3 months.

The concentrated aluminum-zirconium glycine solutions are useful in the formulation of antiperspirant compositions such as solid (stick), roll-on, aerosol, and pump spray compositions. However, because of the presence of water they are most useful in roll-ons and pump sprays.

Although the object of this invention is to produce stable concentrated solutions of aluminum-zirconium glycine, the solutions can be dried to produce a solid aluminum-zirconium glycine salts. The method for drying the concentrated solutions are those known in the art such as spray drying, evaporation, rotary drying, vacuum and others. Spray drying in the preferred technique for producing the solid aluminum-zirconium glycine.

It is feasible to produce activated solid aluminum-zirconium glycine salts when the solution is dried. This is achieved by blending the zirconium-glycine solution with an activated aluminum chlorohydrate solution to result in a concentrated activated aluminum-zirconium glycine solution. This solution is dried to a solid to result in the activated aluminum-zirconium glycine salt. The solid aluminum-zirconium glycine salts are also useful in antiperspirant compositions such as solids, roll-ons, aerosols and pump sprays.

So that those skilled in the art can understand and appreciate the invention taught herein, the following examples are presented, it being understood that these examples should not be used to limit the scope of this invention over the limitation found in the claims attached hereto.

ANALYTICAL

The viscosity of the solutions was determined by using a Brookfield Viscometer model LVTD, Stroughton, Mass. The spindle used was LV spindle #2 at 30 rpm's, with the reading taken after one minute. The samples were all measured at 20° C.

The percent solids of the solution was determined by taking a pre-weighed sample and placing it in an 105° C. forced draft oven for 18 hours or until the weight remains constant. The sample is placed in a desiccator until cooled to room temperature and re-weighed. The % solids (or % non-volatile) is calculated from the following formula $$\text{Solids, \%} = \frac{(C - A)(100)}{(B - A)}$$

where
A = Tare weight of the dish
B = Weight of the dish and sample
C = Weight of dish and sample after heating The Size Exclusion Chromatographic Test used herein is described in European Patent Application 0 256 831, herein incorporated by reference. Sample preparation for the comprises diluting the solution with 0.01N HCl until the solids concentration is 20 percent. The sample is shaken. 2 to 3 ml of the liquid are drawn off and filtered through a 5 ml syringe filter. In order to assure freshness, the sample must be injected within 5 minutes after preparation. The injected sample size is 2.0 microliters. In the instant application, Peak 4 corresponds with Band III, Peak 3 corresponds with Band II and Peaks 1 & 2 corresponds with Band I defined in European Patent Application 0 256 831.

EXAMPLE 1

3.4 grams of deionized water and 26 grams of hydrochloric acid (30% Cl) were combined in a beaker. While mixing, 44.6 grams of zirconium carbonate ($ZrOCO_3$, 30% Zr) was slowly added and the mixture was heated to a boil. The mixture was held at boiling temperature for 1 hour. The mixture was cooled to 50° C. and 6.0 grams of glycine was added and thoroughly mixed. The solution was allowed to cool to room temperature and 120 grams of aluminum chlorohydrate (12.5% aluminum, 8.2% chlorine) was added and thoroughly mixed. The viscosity was 20 centipoise. The solution has was stable for 12 months at room temperature.

EXAMPLE 2

100 grams of deionized water and 440 grams of hydrochloric acid (32% Cl) were combined in a beaker. While mixing, 1,100 grams of zirconium carbonate ($ZrOCO_3$, 30% Zr) was slowly added and the mixture was heated to 95° C. The mixture was held at 95° C. for ½ hour. The mixture was cooled to 50° C. and 300 grams of glycine was added and thoroughly mixed. Size exclusion chromatographic analysis showed that there was 35.99 area percent of Peaks 1&2. The solution was allowed to cool to room temperature and 3,000 grams of aluminum chlorohydrate was added and thoroughly mixed. The viscosity was 15 centipoise. The solution has been stable for 3 months at room temperature.

EXAMPLE 3

870 grams of deionized water and 2,000 grams of zirconyl chloride ($ZrOCl_2$, 26% Zr, 20% Cl) were combined in a beaker. While mixing, 530 grams of zirconium carbonate ($ZrOCO_3$, 30% Zr) was slowly added and the mixture was heated to a 90°-100° C. The mixture was held at boiling temperature for ½ hour. The mixture was cooled to 60° C. and 600.0 grams of glycine was added and thoroughly mixed. The solution was allowed to cool to room temperature and 6,000 grams of aluminum chlorohydrate (12.5% aluminum, 8.2% chlorine) was added and thoroughly mixed. The viscosity was 18 centipoise. The solution was stable for 3 months at room temperature.

EXAMPLE 4

24 grams of deionized water and 63 grams of hydrochloric acid (32% Cl) were combined in a beaker. While mixing, 165 grams of zirconium carbonate ($ZrOCO_3$, 30% Zr) was slowly added and the mixture was heated to 95° C. The mixture was held at 95° C. for ½ hour. The mixture was cooled to 50° C. and 48 grams of glycine was added and thoroughly mixed. Size exclusion chromatographic analysis showed that there was 35.19 area percent of Peaks 1&2. The solution was allowed to cool to room temperature and 450 grams of aluminum chlorohydrate was added and thoroughly mixed. The viscosity was 20 centipoise. The solution has been stable for 3 months at room temperature.

EXAMPLE 5

This example shows the changes in the zirconium glycine solution as a result of heating. Samples comprised of zirconium carbonate, distilled water and hydrochloric acid were heated at the specified temperature (70°-90° C.) for the specified period of time (0.5-2 hours). The sample was cooled to 50° C. and glycine was added. For comparison a sample was prepared as above except that it was not heated prior to the addition of the glycine. The samples were then analyzed by Size Exclusion Chromatography to determine the degree of complexing. Results of the size exclusion chromatography are given Table 1. The Peak % represent the area percent.

TABLE 1

| Peaks: | 1 & 2 | 3 | 4 | 5 | 6 | 7 |
|---|---|---|---|---|---|---|
| Unheated | 8.26 | 3.67 | 3.69 | 0.52 | 33.73 | 50.12 |
| Temp = 70° C. | | | | | | |
| Time  0.5 hr | 21.6 | nd | 2.29 | 0.71 | 14.82 | 60.55 |
| 1.0 | 31.21 | nd | nd | 1.01 | 14.32 | 53.45 |
| 2.0 | 36.76 | nd | nd | 1.25 | 14.58 | 47.41 |
| Temp = 80° C. | | | | | | |

TABLE 1-continued

| Peaks: | 1 & 2 | 3 | 4 | 5 | 6 | 7 |
|---|---|---|---|---|---|---|
| Time 0.5 hr | 36.93 | nd | nd | 0.74 | 12.66 | 49.68 |
| 1.0 | 32.19 | nd | nd | 0.70 | 14.22 | 52.89 |
| 2.0 | 35.66 | nd | nd | nd | 15.26 | 49.08 |
| Temp = 90° C. | | | | | | |
| Time 0.5 hr | 35.30 | nd | nd | 1.30 | 13.89 | 49.51 |
| 1.0 | 33.43 | nd | nd | 1.11 | 15.20 | 50.26 |
| 2.0 | 42.48 | nd | nd | 1.30 | 13.85 | 42.38 | nd = not detected

COMPARATIVE EXAMPLE 1

This example illustrates the stability of the solutions prepared in U.S. Pat. No. 2,814,584. Two solutions were prepared by the method described in U.S. Pat. No. 2,814,584 Example 1 at 50% solids. Within 2 weeks at room temperature the solutions became unstable and precipitated solids.

What is claimed is:
1. A method for producing concentrated aluminum-zirconium glycine solutions consisting essentially of
   (A) forming a zirconium chloride complex by heating aqueous zirconium chloride at 70°-95° C. for 0.5 to 2 hours, wherein the solution is agitated during the heating period, and where the zirconium chloride complex comprises 17-20% by weight zirconium and 7-10% by weight chlorine;
   (B) cooling the solution of (A) down to 50°-70° C.;
   (C) adding glycine to the zirconium complex of (B) that is at a temperature range of 50°-70° C. such that coordinate bonds form between the zirconium and glycine, wherein the added glycine is about 13-15% by weight of the total solution, and the final ratio of zirconium to glycine is 0.8:1 to 1.2:1;
   (D) cooling the solution of (C) down to room temperature; and
   (E) blending the resulting solution of (D) that is at room temperature with a 50% by weight aqueous aluminum chlorohydrate solution, wherein the weight ratio of the solution of (D) to said aluminum chlorohydrate solution is 1:1 to 2:3, and wherein the final solution consists essentially of 45-50% by weight solids and has a viscosity of less than 150 centipoise over a period of at least 3 months.
2. A method as claimed in claim 1 wherein the aqueous aluminum chlorohydrate solution contains 50% by weight solids.
3. A method for producing concentrated aluminum-zirconium glycine salts consisting essentially of
   (A) forming a zirconium chloride complex by heating aqueous zirconium chloride at 70°-95° C. for 0.5 to 2 hours, wherein the solution is agitated during the heating period, and where the zirconium chloride complex comprises 17-20% by weight zirconium and 7-10% by weight chlorine;
   (B) cooling the solution of (A) down to 50°-70° C.;
   (C) adding glycine to the zirconium complex of (B) that is at a temperature range of 50°-70° C. such that coordinate bonds form between the zirconium and glycine, wherein the added glycine is about 13-15% by weight of the total solution, and the final ratio of zirconium to glycine is 0.8:1 to 1.2:1;
   (D) cooling the solution of (C) down to room temperature;
   (E) blending the resulting solution of (D) that is at room temperature with a 50% by weight aqueous aluminum chlorohydrate solution, wherein the weight ratio of the solution of (D) to said aluminum chlorohydrate solution is 1:1 to 2:3, and wherein the final solution consists essentially of 45-50% by weight solids and has a viscosity of less than 150 centipoise over a period of at least 3 months;
   (F) drying the blend produced in (E) to a solid; and
   (G) recovering the aluminum-zirconium glycine salt.
4. A method as claimed in claim 3 wherein the aqueous aluminum chlorohydrate solution is an activated aluminum chlorohydrate solution.
5. A method as claimed in claim 3 wherein the blend produced in (E) is dried by spray drying.

* * * * *